(12) United States Patent
Seo

(10) Patent No.: US 8,381,312 B2
(45) Date of Patent: Feb. 26, 2013

(54) WELDING MASK

(76) Inventor: Won Su Seo, Gwang Myeong (KR)

( * ) Notice: Subject to any disclaimer, the term of this patent is extended or adjusted under 35 U.S.C. 154(b) by 126 days.

(21) Appl. No.: 12/746,783

(22) PCT Filed: Feb. 4, 2008

(86) PCT No.: PCT/KR2008/000663
§ 371 (c)(1),
(2), (4) Date: Jun. 8, 2010

(87) PCT Pub. No.: WO2009/099257
PCT Pub. Date: Aug. 13, 2009

(65) Prior Publication Data
US 2010/0287676 A1 Nov. 18, 2010

(51) Int. Cl.
*A61F 9/06* (2006.01)
(52) U.S. Cl. .............................................. 2/8.4
(58) Field of Classification Search ............... 2/7, 8.1, 2/8.2, 8.3, 8.4, 6.5, 424, 434
See application file for complete search history.

(56) References Cited

U.S. PATENT DOCUMENTS

| | | | | |
|---|---|---|---|---|
| 2,360,101 A * | 10/1944 | Bowers | ................................ | 2/8.1 |
| 2,384,765 A * | 9/1945 | O'Reilly | ............................. | 2/8.3 |
| 2,433,164 A * | 12/1947 | Shields | ............................... | 2/8.1 |
| 2,736,027 A * | 2/1956 | Parmelee | ............................ | 2/8.1 |
| 3,490,071 A * | 1/1970 | Marshall | ............................. | 2/8.3 |
| 3,753,482 A * | 8/1973 | Brown et al. | .............. | 400/134.1 |
| 4,185,329 A * | 1/1980 | Sarazen | ............................... | 2/8.3 |
| 4,853,973 A * | 8/1989 | Boochard | ........................... | 2/8.1 |
| 4,875,235 A * | 10/1989 | Kuhlman | ............................ | 2/8.3 |
| 5,140,707 A * | 8/1992 | Johnson | .............................. | 2/8.1 |
| 5,571,217 A * | 11/1996 | Del Bon et al. | ........................ | 2/9 |
| 6,008,466 A * | 12/1999 | Hosoda | ..................... | 219/121.62 |
| 6,973,672 B2 * | 12/2005 | Huh | .................................... | 2/8.1 |
| 7,284,281 B2 * | 10/2007 | Huh | .................................... | 2/8.2 |
| 7,308,719 B2 * | 12/2007 | Huh | .................................... | 2/8.2 |
| 7,937,775 B2 * | 5/2011 | Manzella et al. | .............. | 2/171.3 |

* cited by examiner

*Primary Examiner* — Shelley Self
*Assistant Examiner* — Andrew Sutton
(74) *Attorney, Agent, or Firm* — Galgano & Associates, PLLC; Thomas M. Galgano; Jessica G. Bower

(57) ABSTRACT

A welding mask including a mask body for covering an entire face of a wearer having an opening portion corresponding to eyes of the wearer thereof; a rotatable cover rotationally coupled to a front of the mask body upward and downward; a shading filter mounted on the rotatable cover so as to shade a light generated during welding operation thereof; an elastic coupling means for rotationally coupling the rotatable cover to both side surfaces of the mask body upward; and a fixing means for fixing the rotatable cover or releasing a fixing status thereof formed at one side of the mask body. In addition, a window is further formed at the rear portion of the rotatable cover having the shading filter, thereby improving operation efficiency.

6 Claims, 3 Drawing Sheets

WELDING MASK

TECHNICAL FIELD

The present invention relates to a welding mask, and more particularly to a welding mask, in that the rotatable cover is rotationally coupled to a front of the mask body and a window is further formed at the rear side of the rotatable cover, so that various works can be performed without repeating the wearing and undressing of the welding helmet, whereby improving operation efficiency.

BACKGROUND ART

Generally, a term "welding" means that metals are heated and dissolved by using a fusibility thereof, thereby adhering to each other.

During the welding process, since strong rays are emitted and sparks fly up, it can bring about a damage of eyesight or eyeball owing to the blazing rays or the sparks.

In order to protect the eyes of the worker from the blazing and harmful rays, a welding helmet provided with a shading filter including a LCD, a glass, electronic circuits, a controller and a power supply device is widely used.

FIG. 1 is a schematic perspective view illustrating a conventional welding helmet.

As shown in FIG. 1, the welding helmet includes a welding mask 10 for covering the entire face of the wearer, a wearing band for wearing the welding mask 10 on a head of the wearer and rotating the welding mask 10 at a predetermined angle upward and downward and coupled to the welding mask 10 through a rotating axis 11, a LCD cartridge 12 for protecting the eye of the wearer from the strong rays generated during the operation thereof and formed at a location corresponding to the eye of the wearer, and a front cover 13 for protecting the LCD cartridge 12 and formed at the front side of the LCD cartridge 12.

According to the conventional welding helmet, the strong rays generated during the welding process can be blocked by the LCD cartridge 12.

By the way, The strong rays are not generated during other operations or moving excepting for the welding operation. Accordingly, it is necessary to undress the welding helmet during other operations excepting for the welding operation. However, in this case, since the welding helmet should be again worn for welding operation, there is an inconvenience owing to the repeated wearing and undressing.

Also, the wearer undresses the welding helmet during other operations except the welding operation. At this time, it can bring about the damage of the eye or face of the wearer due to the broken piece generated during a grinding operation.

Moreover, in a case of the contamination of the shading filter mounted on the welding mask of the conventional welding helmet, the failure of the circuit portion, or the exchange of the battery for power supply, since it is necessary to undress the welding helmet and then, release the coupling statues of the welding mask, there are problems in that the entire shading filter is separated from the welding helmet in order to exchange it and the exchange of the shading filter is impossible in a state of wearing the welding helmet.

DISCLOSURE OF INVENTION

Technical Problem

Accordingly, the present invention has been made to solve the above-mentioned problems occurring in the prior art, and an object of the present invention is to provide a welding mask in that a rotatable cover is rotationally coupled to the side of the mask body upward and downward and a window is formed at the mask body corresponding to the eyes of the wearer, so that the rotatable cover is upward opened in order to expose the window during other operations excepting for the welding operation and the rotatable cover is again took down in order to block the strong rays during the welding operation, whereby solving the inconvenience owing to the repeated wearing and undressing thereof.

Another object of the present invention is to provide a welding mask in that a lower end portion of the front of the rotatable cover is fixed to the mask body through a button and the rotatable cover is rotationally coupled to both side surfaces of the mask body upward through an elastic coupling means, so that the fixing status of the rotatable cover is released through a simple button operation and then, upward opened through the elastic power of the elastic coupling means to maintain the opening status thereof, thereby ensuring a visual field without being manually operated and improving an convenience of the work on account of an easy opening operation of the rotatable cover.

Further another object of the present invention is to provide a welding mask in that a front cover for selectively opening and closing the shading filter is coupled to one side of the rotatable cover through a hinge axis, so that the shading filter can be easily replaced and repaired.

Technical Solution

To accomplish the object, the present invention provides a welding mask comprising: a mask body for covering an entire face of a wearer having an opening portion corresponding to eyes of a wearer thereof; a rotatable cover rotationally coupled to a front of the mask body upward and downward; a shading filter mounted on the rotatable cover so as to shade a light generated during welding operation thereof; an elastic coupling means for rotationally coupling the rotatable cover to both side surfaces of the mask body upward; a fixing means for fixing the rotatable cover or releasing a fixing status thereof formed at one side of the mask body and having a spring receiving portion for receiving the spring, a mounting hole located at an upper surface thereof, and a push plate elastically coupled to the mask body through a spring; and a latching protrusion for attaching and deattaching to the mounting hole formed at a lower end portion of the front of the rotatable cover.

Preferably, the welding mask further comprises a window formed at the opening portion of the mask body corresponding to eyes of the wearer.

Preferably, the elastic coupling means comprises a spring having two bending portions formed at both end portions thereof and one bending portion coupled to the mask body; a knob holder having a through hole in the center to be coupled to a coupling hole of the rotatable cover, opening in the bottom for receiving the spring therein and a plurality of latching projections formed along the girth of the through hole; a knob having a circle plate having a plurality of latching grooves corresponding to the plurality of latching projections formed at a lower portion thereof and a column integrally formed at the lower portion thereof and having a vertical groove for inserting and fixing one end portion of the spring in a central portion thereof and a bolt coupling portion formed at a central portion of the vertical groove; and a washer having a through hole for inserting the bolt therein fixed and coupled to the column and the knob holder is coupled to a coupling hole of the rotatable cover, thereby being rotated in company with the rotatable cover during rotating of the knob holder.

Preferably, a front cover for selectively opening and closing the shading filter is coupled to one side of the rotatable cover through a hinge axis.

Advantageous Effects

In the welding mask according to the present invention, there are effects in that the rotatable cover is rotationally coupled to the side of the mask body upward and downward and the window is formed at the mask body corresponding to the eyes of the wearer, so that the rotatable cover is upward opened in order to expose the window during other operations excepting for the welding operation and the rotatable cover is again took down in order to block the strong rays during the welding operation, whereby solving the inconvenience owing to the repeated wearing and undressing thereof.

Also, there is another effect in that the lower end portion of the front of the rotatable cover is fixed to the mask body through the button and the rotatable cover is rotationally coupled to both side surfaces of the mask body upward through the elastic coupling means, so that the fixing status of the rotatable cover is released through the simple button operation and then, upward opened through the elastic power of the elastic coupling means to maintain the opening status thereof, thereby ensuring a visual field without being manually operated and improving an convenience of the work on account of an easy opening operation of the rotatable cover.

Also, there is further another effect in that the front cover for selectively opening and closing the shading filter is coupled to one side of the rotatable cover through the hinge axis, so that the shading filter can be easily replaced and repaired.

BRIEF DESCRIPTION OF THE DRAWINGS

The above as well as the other objects, features and advantages of the present invention will be more apparent from the following detailed description taken in conjunction with the accompanying drawings, in which.

BEST MODE FOR CARRYING OUT THE INVENTION

A preferred embodiment of the invention will be described in detail below with reference to the accompanying drawings.

Figure 1:
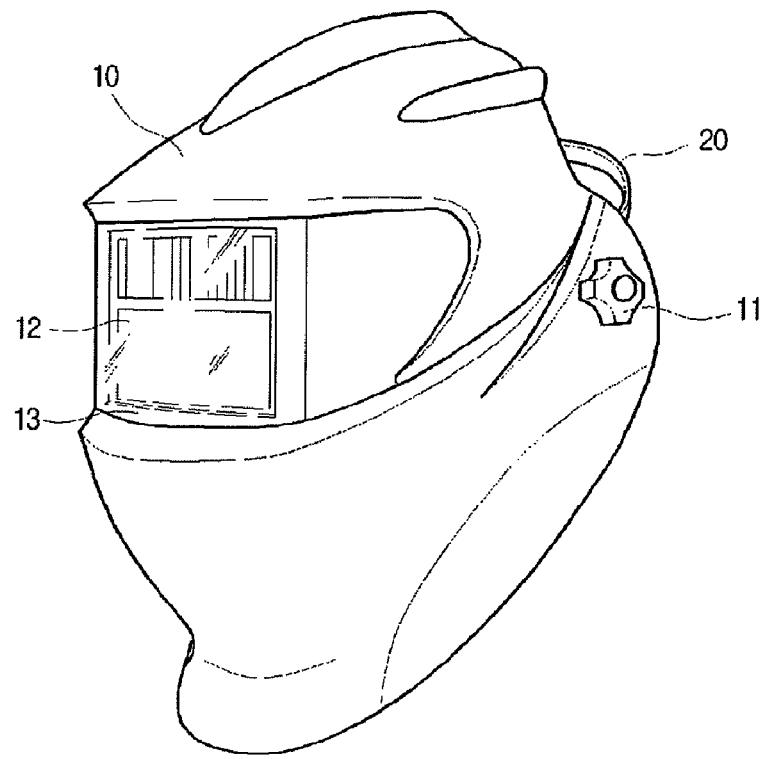
FIG. 1 is a schematic perspective view illustrating a conventional welding helmet.
Figure 2:
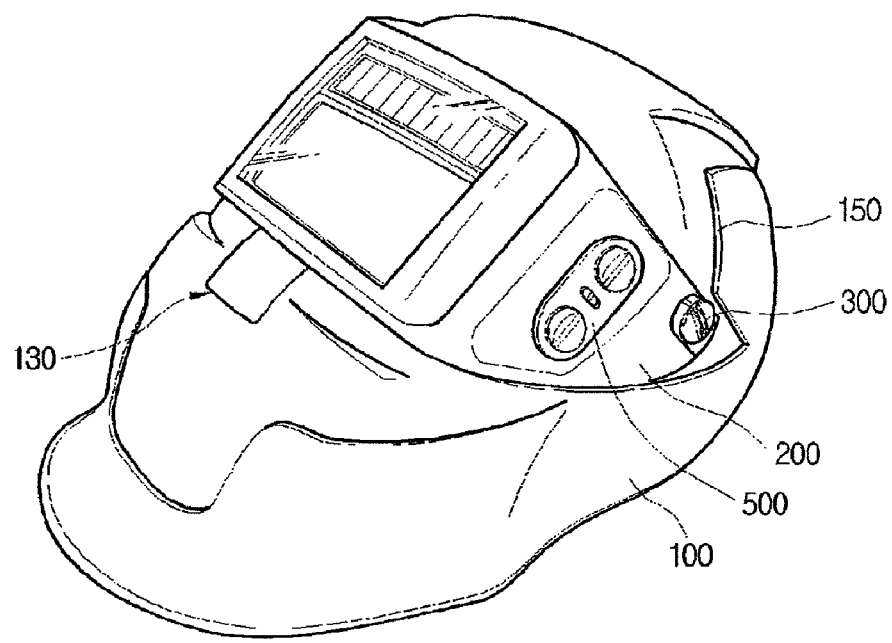
FIG. 2 is a schematic perspective view illustrating a welding mask according to one embodiment of the present invention.
Figure 3:
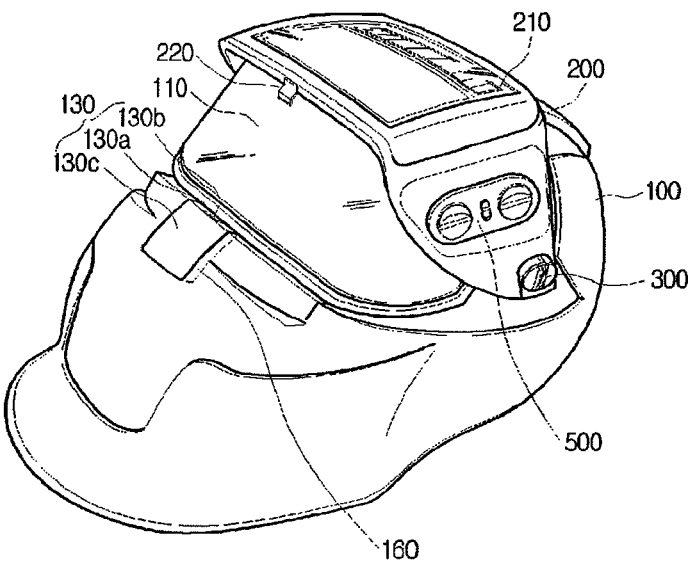
FIG. 3 is a schematic perspective view illustrating a status of rotating a rotatable cover of FIG. 2.

FIG. 2 is a schematic perspective view illustrating a welding mask according to one embodiment of the present invention and FIG. 3 is a schematic perspective view illustrating a status of rotating a rotatable cover of FIG. 2.

According to the welding mask according to one embodiment of the present invention, the welding mask is coupled to a wearing band for putting on user's head through a rotation axis to constitute a welding helmet.

As shown in the drawings, the welding mask according to one embodiment of the present invention includes a mask body 100, a rotatable cover 200, a shading filter 210, and a window 110.

The mask body 100 for covering the entire face of the wearer includes an opening portion corresponding to eyes of the wearer thereof. Also, the rotatable cover 200 is rotationally coupled to the front of the mask body 100 upward and downward.

The shading filter 210 is mounted on the rotatable cover 200 so as to shade the light generated during the welding operation thereof. Also, a controller 500 for controlling a sensitivity, a light-shading, and an opening delay of the shading filter 210 is formed at one side surface of the rotatable cover 200.

The window 110 is formed at the opening portion of the mask body 100 corresponding to the eyes of the wearer, so that it can serve to prevent the damage of the eye or face of the wearer due to the broken piece generated during the grinding operation except the welding. Here, the window 110 includes two coupling grooves, which are coupled to two coupling latches formed at inner surfaces of the mask body 100, formed at both end portions thereof, so that it can be attached and deattached to the mask body 100. Preferably, the material of the window 110 is a synthetic resin for easily attaching and deattaching to the mask body 100.

That is, in the conventional art, besides the welding operation, the grinding operation is conducted in a state of getting out of his welding helmet owing to an unnecessary shading operation of the shading filter 210. Accordingly, the broken piece generated from the grinding operation can bring about the damage of the eye or face of the wearer.

However, in the present invention, the grinding operation can be performed in a state that the rotatable cover 200 having the shading filter 210 is rotationally moved upward. Accordingly, the window 100 serves to block the broken pieces, so that the eye or face of the wearer can be protected.

In the meantime, the rotatable cover 200 is rotationally coupled to both side surfaces of the mask body 100 upward through an elastic coupling means 300. Also, the rotatable cover 200 is temporarily fixed to the mask body 100 through a button 130. That is, a push plate 130*c* of the button 130 having a mounting hole 130*b* located at the upper surface thereof is elastically coupled to the mask body 100 through a spring 130*a*.

Here, the mask body 100 further includes a spring receiving portion 160 for receiving the spring 130*a*. Also, the spring 130*a* received in the receiving portion 160 is coupled to the mask body 100 through a bolt (not shown) penetrated through a back surface of the mask body 100.

Also, a latching protrusion 220 for inserting into the mounting hole 130*b* is formed at a lower end portion of the front of the rotatable cover 200. Hence, the latching protrusion 220 is inserted into the mounting hole 130*b*, so that the rotatable cover 200 is temporarily fixed to the mask body 100 without being rotated.

Accordingly, where the push plate 130*c* is pressed, the fixing state of the rotatable cover 200 is released, thereby opening the window 110.

In other words, when the push plate 130*c* is pressed, the latching protrusion 220 is separated from the mounting hole 130*b*, so that the temporary fixing state of the rotatable cover 200 is released and the rotatable cover 200 is upwardly rotated through the elastic coupling means 300, thereby opening the window 110.

In the meantime, a stopper 150 for restricting the rotating angle of the rotatable cover 200 can be protruded from the upper surface of the window 100.

Figure 4:
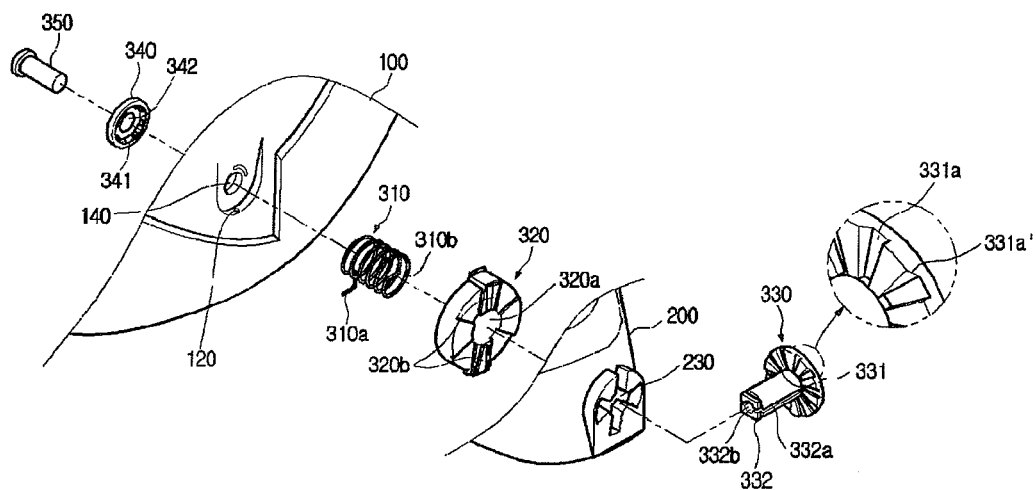
FIG. 4 is an exploded perspective view illustrating a coupling relation between the elastic coupling means of FIG. 2.

FIG. 4 is an exploded perspective view illustrating a coupling relation between the elastic coupling means of FIG. 2.

As shown in FIG. 4, the elastic coupling means 300 includes a spring 310, a knob holder 320, a knob 300, and a washer 340.

The spring 310 having an elastic force of restitution includes two bending portions 310a and 310b formed at both end portions thereof.

Also, the knob holder 320 has shape corresponding to coupling hole 230 of rotatable cover 200 to couple to be coupled to coupling hole 230 of ratatable cover 200. the knob holder 320 has opening in the bottom for receiving spring 310, through hole 320a in the center and a plurality of latching projections 320b formed along the girth of the through hole 320a.

The knob 330 for inserting and fixing one end portion of the spring 310 is coupled to one side of the knob holder 320, thereby being rotated in company with the knob holder 320. That is, The knob 330 includes a circle plate 331 having a plurality of latching grooves 331a corresponding to the plurality of latching projections 320b formed at a lower portion thereof and a column 332 integrally formed at the lower portion thereof and having a vertical groove 332a for inserting and fixing one end portion of the spring 310 in a central portion thereof and a bolt coupling portion 332b formed at a central portion of the vertical groove 332a.

Here, it is preferred that each latching groove 331a of The knob 330 includes a slanted surface 331a' slanted upward at a predetermined angle at one side surface thereof.

That is, in order to strength the elastic force of restitution of the spring through the rotation of the knob 330 coupled to the knob holder 320, it is necessary for each latching projections 320 to slide along the slanted surface of the latching groove 331a. Accordingly, it is preferred that the upward slanted surface 331a' is formed at one side surface thereof.

The washer 340 having a through hole 341 for inserting the bolt 350 therein is fixed and coupled to the column 332 and a plurality of protrusions 341 protruded in the inner direction of the upper opening surface.

The coupling relation between the elastic coupling means 300 will be described in detail below.

Firstly, one bending portion 310a of the spring 310 is inserted into the through hole 120 of the mask body 100 and a part of the spring is received in the knob holder 320.

Then, the knob holder 320 is coupled to the coupling hole 230 formed at the inner end portion of the rotatable cover 200, so that it is rotated in company with the rotatable cover 200. Here, each latching projection 320b is protruded toward the outside of the coupling hole 230 of the rotatable cover 200.

Continuously, The knob 330 is coupled to the knob holder 320 through the coupling hole 230 of the rotatable cover 200 and the through hole 320a of the knob holder 320 so that the bending portion 310b of spring 310 is inseted into the vertical groove 332a. Here, The knob 330 can be rotated in company with the knob holder 320 or The knob 330 can be rotated apart from the knob holder 320.

Finally, the washer 340 is integrally coupled to the knob 330 through the bolt 350, which is penetrated through the through hole 341 of the washer 340 and inserted into the bolt coupling portion 332b located at the central portion of the column 332.

The operation of the welding mask according to the coupling relation between the elastic coupling means 300 will be described in detail below.

Firstly, the knob is forward rotated, so that it grants the elastic power to the spring 310, which is coupled between the mask body 100 and the vertical groove 332a of the knob 330.

Then, the latching projections 320b are inserted into the latching grooves 331a, so that the knob 320 is coupled to the knob holder 320.

Continuously, the latching protrusion 220 formed at the lower end portion of the rotatable cover 200 is inserted into the mounting hole 130b, so that the rotatable cover 200 is fixed to the mask body 100, thereby covering the window 110.

Here, if the push plate 130c is pressed, the latching protrusion 220 is separated from the mounting hole 130b and the rotatable cover 200 is upwardly rotated through the elastic force of restitution of the spring 310.

In other words, since the spring has the elastic power through a compression thereof, the latching protrusion 220 is separated from the mounting hole 130b, so that the knob 330 is rotated toward the rear of the mask body 100 through the elastic force of restitution of the spring 310, thereby the knob holder 320 coupled to the knob 330 can be backward rotated.

After all, the rotatable cover 200 having the inserted knob holder 320 is upward rotated, thereby opening the window 110.

In the meantime, if the rotatable cover 200, which is upward rotated, is downward rotated through an external force of a worker and the latching protrusion 220 is inserted and fixed into the mounting hole 130b, the knob holder 320 is forward rotated and the knob 330 is forward rotated in company with the knob holder 320.

Accordingly, since the spring 310 has the elastic power through the compression thereof, the rotatable cover 200 is temporarily fixed to the mask body 100 through the coupling of the button 130 while it has the intention of upward rotating owing to the elastic force of restitution thereof.

Figure 5:
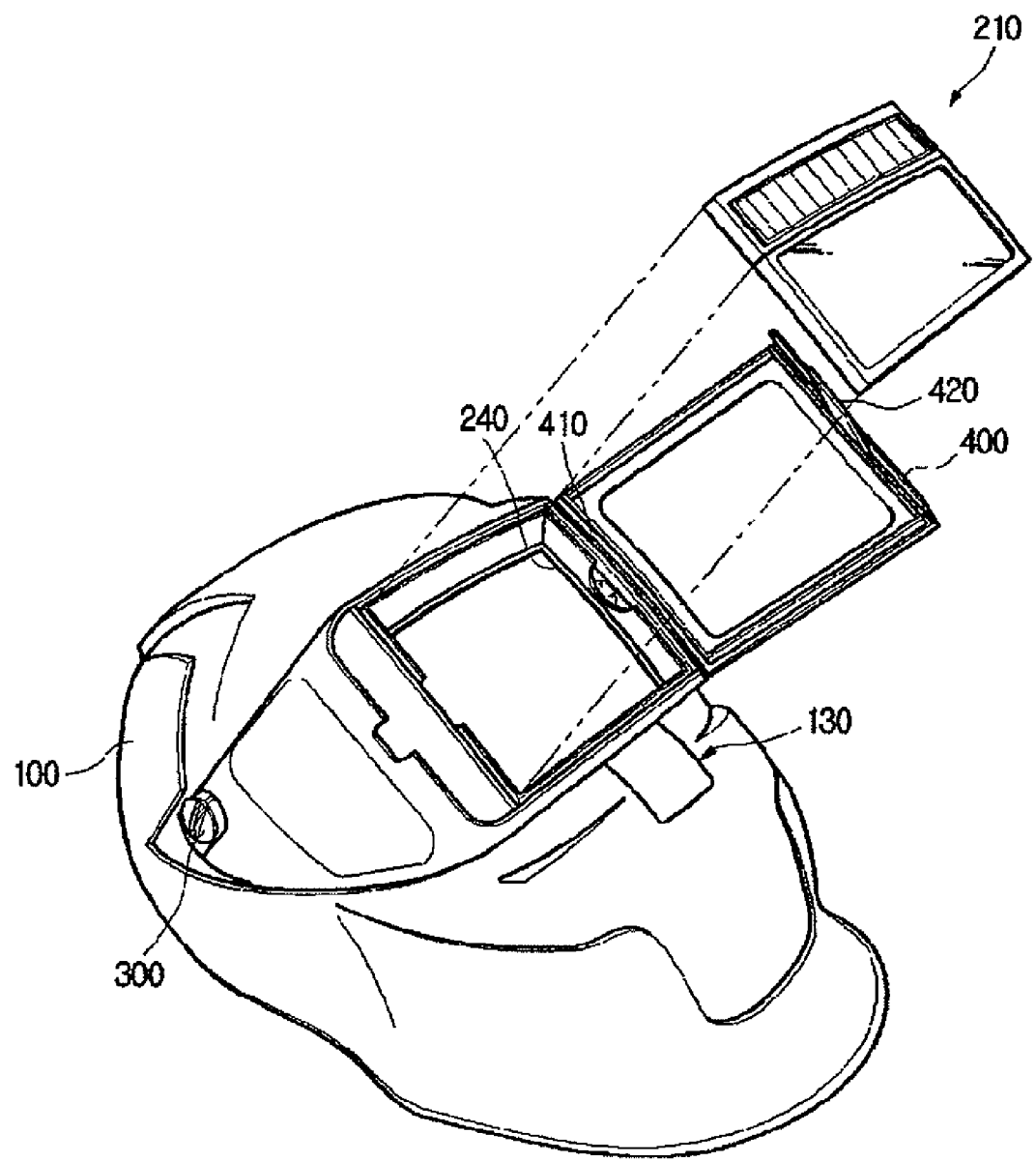
FIG. 5 is a schematic perspective view illustrating a welding mask according to another embodiment of the present invention.

FIG. 5 is a schematic perspective view illustrating a welding mask according to another embodiment of the present invention. The explanation on the same elements as the first embodiment of the present invention is omitted here.

The welding mask according to another embodiment of the present invention further includes a seating groove 230 for mounting the shading filter 210 on the front surface of the rotatable cover 200 and a front cover 400 for selectively opening and closing the shading filter 210 coupled to one side of the rotatable cover 200 through a hinge axis 410.

Also, a latching protrusion 420 formed at the front cover 400 is attached and deattached to a latching groove formed at one side of the rotatable cover 200, thereby opening and closing the front cover 400.

According to another embodiment of the present invention, the front cover 400 is further formed at the front surface of the rotatable cover 200 having the shading filter 210, so that the shading filter 210 can be easily replaced and repaired.

While this invention has been described in connection with what are presently considered to be the most practical and preferred embodiments, it is to be understood that the invention is not limited to the disclosed embodiments and the drawings, but, on the contrary, it is intended to cover various modifications and variations within the spirit and scope of the appended claims.

Industrial Applicability

The present invention relates to a welding mask capable of ensuring the safety of the work and solving the inconvenience owing to the repeated wearing and undressing of a welding helmet, thereby improving an convenience of the work.

The invention claimed is:
1. A welding mask, comprising:
a mask body for covering an entire face of a wearer having an opening portion corresponding to eyes of a wearer thereof;

a rotatable cover rotationally coupled to a front of the mask body, which is pivotable in an upward and downward direction;

a shading filter mounted on the rotatable cover so as to shade a light generated during welding operation thereof;

an elastic coupling means for rotationally coupling the rotatable cover to both side surfaces of the mask body and providing elastic force to normally urge the rotatable cover in said upward direction, said elastic coupling means comprising a spring having two bending portions formed at both end portions thereof and one bending portion coupled to the mask body; a knob holder having a through hole in the center to be coupled to a coupling hole of the rotatable cover, opening in the bottom for receiving the spring therein and a plurality of latching projections formed along the girth of the through hole; a knob having a circle plate having a plurality of latching grooves corresponding to the plurality of latching projections formed at a lower portion thereof and a column integrally formed at the lower portion thereof and having a vertical groove for inserting and fixing one end portion of the spring in a central portion thereof and a bolt coupling portion formed at a central portion of the vertical groove; and a washer having a through hole for inserting the bolt therein fixed and coupled to the column, the knob holder being coupled to a coupling hole of the rotatable cover, thereby being rotated in company with the rotatable cover during rotating of the knob holder;

a fixing means for fixing the rotatable cover or releasing a fixing status thereof formed at one side of the mask body and having a spring receiving portion for receiving the spring, a mounting hole located at an upper surface thereof, and a push plate elastically coupled to the mask body through a spring;

a latching protrusion for attaching and deattaching to the mounting hole formed at a lower end portion of the front of the rotatable cover; and a window formed at the opening portion of the mask body corresponding to eyes of the wearer.

2. The welding mask as claimed in claim 1, wherein a front cover for selectively opening and closing the shading filter is coupled to one side of the rotatable cover through a hinge axis.

3. A welding mask, comprising:

a mask body for covering an entire face of a wearer, defining an opening therein which is disposed in front of eyes of a wearer, said mask body having a front portion and two opposite side surfaces;

a pivotable cover, pivotably coupled to said mask body, and having a lower edge, said pivotable cover being moveable between a first lower position wherein said pivotable cover overlies said opening in said mask body and a second upper position wherein said pivotable cover is pivoted in an upward direction from said first lower position, to expose at least a portion of said opening in said mask body, and in a downward direction from said second upper position to said first lower position;

a shading filter mounted on said pivotable cover to shade a light generated during a welding operation;

elastic coupling means for pivotably coupling said pivotable cover to both of said side surfaces of said mask body, wherein said elastic coupling means provides an elastic force to normally urge said pivotable cover in said upward direction;

a releasable locking means disposed on said mask body, for locking said pivotable cover in said first lower position and releasing said pivotable cover from said first lower position to permit said pivotable cover to move in said upward direction to said second upper position, said releasable locking means having a spring and a spring receiving portion for receiving said spring, a push plate having an upper surface, said push plate being elastically coupled to said mask body through said spring and a mounting hole formed in said upper surface of said push plate; and a latching tab projecting downwardly from said lower edge of said pivotable cover, said latching tab removably receivable in said mounting hole of said releasable locking means when said pivotable cover is in said first lower position, wherein when said push plate is pressed, said latching tab is released from said mounting hole, and said pivotable cover automatically pivots in said upward direction from said first lower position to said second upper position via said elastic coupling means.

4. A welding mask as claimed in claim 3, further comprising:

a window formed at said opening of said mask body corresponding to the eyes of the wearer.

5. A welding mask as claimed in claim 4, wherein:

said elastic coupling means comprises:

a spring having two bending portions formed at both end portions thereof and one bending portion coupled to said mask body;

a knob holder having a through hole in the center to be coupled to a coupling hole of said rotatable cover, an opening in the bottom for receiving said spring therein and a plurality of latching projections formed along the girth of said through hole;

a knob having a circle plate having a plurality of latching grooves corresponding to said plurality of latching projections formed at a lower portion thereof and a column integrally formed at said lower portion thereof and having a vertical groove for inserting and fixing one end portion of said spring in a central portion thereof and a bolt coupling portion formed at a central portion of the vertical groove; and a washer having a through hole for inserting said bolt therein fixed and coupled to said column, said knob holder being coupled to a coupling hole of said rotatable cover, thereby being rotated in company with said rotatable cover during rotating of said knob holder.

6. A welding mask as claimed in claim 3, wherein:

a front cover for selectively opening and closing said shading filter is coupled to one side of said rotatable cover through a hinge axis.

* * * * *